United States Patent [19]

Monti-Bloch

[11] Patent Number: 5,303,703
[45] Date of Patent: Apr. 19, 1994

[54] COMBINED NEUROEPITHELIAL SAMPLE DELIVERY ELECTRODE DEVICE AND METHODS OF USING SAME

[75] Inventor: Luis Monti-Bloch, Salt Lake City, Utah

[73] Assignee: Pherin Corporation, Menlo Park, Calif.

[21] Appl. No.: 771,414

[22] Filed: Oct. 3, 1991

[51] Int. Cl.$^5$ .............................................. A61B 5/04
[52] U.S. Cl. .................... 128/642; 128/747; 128/774; 604/35
[58] Field of Search ............. 128/642, 774, 747, 734; 604/35; 606/49, 45

[56] References Cited

U.S. PATENT DOCUMENTS

| | | | |
|---|---|---|---|
| 4,936,301 | 6/1990 | Rexroth et al. | 606/49 |
| 5,122,138 | 6/1992 | Manwaring | 606/49 |

FOREIGN PATENT DOCUMENTS

| | | |
|---|---|---|
| 917822 | 4/1982 | U.S.S.R. |
| 1459647 | 2/1989 | U.S.S.R. |

OTHER PUBLICATIONS

Duchamp-Viret et al., "Olfactory discrimination over a wide concentration range. Comparison of receptor cell and bulb neuron abilities" *Brain Research* (1990) 517:256-262.
Frey, A. H., "Electro-olfactogram technique and interpretation" Contract No. N00014-69-C-0181, AD-705 520, 11 pages total. Applicants have enclosed an abstract due to the poor quality of the microfilm reproduction.
Gesteland et al., "Comments on microelectrodes" *Proceedings of the IRE* (1959) 17:1856-1862.
Gesteland et al., "Chemical transmission in the nose of the frog" *J. Physiol.* (1965) 181:525-559.
Gesteland et al., "Neural coding in olfactory receptor cells" *Handbook of Sensory Physiology* (1974) 4:132-150.
Getchell et al., "Responses of olfactory receptor cells to step pulses of odor at different concentrations in the salamander" *J. Physiol.*, (1978) 272:521-540.
Kobal et al., "Electro-olfactogram (EOG) in man: Intranasal stimulation and recording" *Pflugers Arch.* (1977) 368:R48 (abstract no. 190).
Mackay-Sim et al., "Topographic coding of olfactory quality: Odorant-specific patterns of epithelial responsivity in the salamander" *J. Neurophysiol.* (1982) 48(2):584-596.
Ottoson, D., "Sustained potentials evoked by olfactory stimulation" *Acta Physiol. Scand.* (1954) 32:384-386.
Ottoson, D., "The electro-olfactogram" *Handbook of Sensory Physiology* (1974) 4(1):95-131.
Plattig et al., "Olfactory and gustatory responses in human electroencephalogram (EEG)" *Food Intake and Chemical Senses*, Katsuki et al., Eds., University Park Press, Tokyo, (1977) pp. 51-70.
Takagi, S. F., "EOG problems" *Olfaction and Taste* (1969) 3:71-91.
Thommesen, G. G., "Specificity and distribution of receptor cells in the olfactory mucosa of char (*Salmo alpinus L.*)" *Acta Physiol. Scand.* (1982) 115:47-56.
Tucker et al., "A physiologic and pharmacologic study of olfactory receptors" *Cold Spring Harbor Symposium in Quantitative Biology* (1965) 30:207-215.
Van Drongelen, W., "Unitary recording of near threshold responses of receptor cells in the olfactory mucosa of the frog" *J. Physiol.* (1978) 277:423-435.
Vigouroux et al., "A wide concentration range olfactometer for delivery of short reproducible odor pulses" *J. Neuroscience Methods* (1988) 24:57-63.

*Primary Examiner*—Kyle L. Howell
*Assistant Examiner*—Brian L. Casler
*Attorney, Agent, or Firm*—Heller, Ehrman, White & McAuliffe

[57] ABSTRACT

The invention relates to combined neuroepithelial electrode and sample delivery devices which deliver a stimulant to neuroepithelial tissue and measure the bioelectric response of the tissue to the stimulant. Some devices also include an evacuation catheter which removes the stimulant from a subject immediately after stimulation, thereby limiting the locus of stimulated tissue. The invention also relates to methods of using these devices to stimulate and measure the response of neuroepithelial tissue, particularly the neuroepithelial tissue of the human vomeronasal organ.

34 Claims, 7 Drawing Sheets

COMBINED NEUROEPITHELIAL SAMPLE DELIVERY ELECTRODE DEVICE AND METHODS OF USING SAME

FIELD OF THE INVENTION

This invention relates generally to the fields of neurophysiology and to neurophysiological instrumentation. More particularly this invention relates to devices for delivery of stimulatory compounds to neuroepithelial tissue and to electrodes for measuring changes in bioelectric voltage. More particularly the invention relates to a combined neuroepithelial electrode and sample delivery device and to methods of using the device to deliver a stimulant to neuroepithelial tissue and measuring the bioelectric response of the tissue to the stimulant.

BACKGROUND ART

Electrodes for the study of neurophysiological tissues have been disclosed. Gesteland et al. (*Proceedings of the IRE* (1959) 47:1856) provides a general review of electrodes and suggests the use of Ag-AgCl electrodes (pg. 1857). Electrodes have been used to study olfactory epithelia and the layer of mucus which overlays this tissue. These studies have provided records interpreted as receptor potentials in response to odorous stimulants. This measurement has been termed an "electro-olfactogram" (EOG).

Stimulation and recording of olfactory epithelia in many species have been disclosed. Ag-AgCl, agar-saline electrodes for olfactory measurement are disclosed in Ottoson, D., *Acta Physiol. Scand.* (1954) 32:384, in rabbits; Gesteland, R. C., et al., *J. Physiol.* (1965) 181:525, in frogs; Mackay-Sim, A., et al., *J. Neurophysiol.* (1982) 48:584, in salamanders; and, Thommesen, G., *Acta Physiol. Scand.* (1982) 115:47, in char.

General review of the measurement of electro-olfactograms (EOG) is provided by Takagi, S. F., in *Olfaction and Taste*, Pfaffmann, ed. (1969) 3:71; Ottoson, D., in *Handbook of Sens. Physiol*, (1974) 4:95; and, Gesteland, R. C., in *Handbook of Sens. Physiol.* (1974) 4:132.

Devices for the delivery of vapors, particularly to olfactory epithelia, have also been disclosed. These devices, which generally combine a constant air flow with the ability to introduce liquid odorous compounds in order to form a stimulatory vapor, have been termed "olfactometers" (Tucker, D. and T. Shibuya, *Cold Spring Harbor Symp Quant. Biol.* (1965) 30:207). Vigouroux, M., et al. (*J. Neurosci. Methods* (1988) 24:57) describe a wide concentration range olfactometer for delivery of short reproducible odor pulses.

Plattig, K. H. and G. Kobal (in *Food Intake and Chem. Senses*, Katsuki, Y., et al. eds. (1977) University Park Press, Baltimore pgs. 51-70) describe a device for olfactory stimulation and recording in humans. Since the delivery of stimulus is external to the nose the device is not precise with regard to the region or type of tissue stimulated.

An embodiment of the subject invention relates to the stimulation of a heretofore poorly understood neuroepithelial structure, commonly known as the vomeronasal organ ("VNO"; also known as "Jacobson's organ"). This organ is located bilaterally in the nostrils of most higher animals—from snakes to humans, and has been associated, inter alia, with pheromone reception in certain species (see generally Muller-Schwarze & Silverstein, *Chemical Signals*, Plenum Press, New York (1980)). The VNO is a small nasal organ with a central lumen and a pit opening to the nasal cavity. The VNO is a bilateral structure located supra palatial. The pit is approximately 1 to 1.5 mm in diameter and the lumen is approximately 1 to 1.5 cm deep. The lumen is lined with sensory neuroepithelia which constitute a distinct locus of olfactory receptors. The axons of the VNO neuroepithelia synapse with the auxiliary olfactory bulb and the amygdala, both in the brain, and from there, to the hypothalamus. Johnson, A. et al. (*J. Otolaryngology* (1985) 14:71-79) report evidence for the presence of the vomeronasal organ in most adult humans, but conclude that the organ is probably non-functional. Contravening results which suggest that the VNO is a functional chemosensory receptor are reported by Stensaas, L., et al. (submitted for publication).

SUMMARY OF THE INVENTION

In one embodiment the invention relates to a device for delivering a vapor to neuroepithelial tissue and measuring the neurophysiologic response of the tissue. The device comprises delivery means for continuously providing the vapor to a locus of neuroepithelial tissue; and sensing means for simultaneously measuring neuroepithelial potential of tissue within the locus.

In another embodiment this invention relates to a device comprising a electrode for the measurement of bioelectrical potential, and, a delivery catheter for providing the vapor. The delivery catheter is generally coaxial with and surrounding the electrode.

In another embodiment of the invention the device additionally comprises an evacuation catheter for removing the vapor from the proximity of the neuroepithelial tissue. The evacuation catheter is generally coaxial with and surrounding the delivery catheter.

Another embodiment is a method of delivering a vapor to neuroepithelial tissue within the lumen of a human vomeronasal organ and measuring the neurophysiologic response of the tissue. The method comprises the following steps: providing a device with a delivery means which has an output end and a sensing means which has a recording end; placing the output end and recording end of the device within the lumen of the vomeronasal organ; continuously delivering the vapor within the lumen; and simultaneously recording the bioelectric response.

Another embodiment is a method of delivering a vapor containing a stimulant to neuroepithelial tissue of a subject and measuring bioelectric response. The method comprises a first step of providing a device which is an embodiment of the invention, namely, a device comprising an electrode, an amplifying means, a delivery catheter, vapor delivery source, an evacuation catheter, and a suction means. The additional steps of the method are placing the electrode in contact with a neurophysiological tissue, delivering the vapor containing stimulant, recording the bioelectric response and removing the vapor containing stimulant.

In another embodiment the delivery, recording and removal are continuous.

It is an object of the invention to provide a compact, combined electrode and vapor delivery device which, when coupled to a signal amplifier and recorder, as well as a vapor delivery source, can deliver a stimulatory vapor to a discrete locus of neuroepithelial tissue and record the bioelectric response of a subset of the stimulated locus. In some cases, the stimulated locus is no more than a few millimeters in diameter and the recorded subregion is a smaller area generally central to the stimulated tissue.

It is another object of the invention to provide a device which additionally removes the stimulatory vapor such that neither proximal nor distal neuroepithelial tissue is exposed to the vapor.

It is yet another object of the invention to provide a device in which the functions, namely delivery, recording and removal are provided continuously.

It is another object of the invention to provide a method of delivering a stimulatory vapor to a limited region of a specific neuroepithelial tissue without stimulating distal tissues, and to measure the response of the stimulated region. Particularly, it is an object of the invention to provide a device and method of specifically stimulating and measuring the response of the neuroepithelial tissue of a vomeronasal organ (VNO), most particularly the VNO of a human subject.

DETAILED DESCRIPTION

Figure 1:
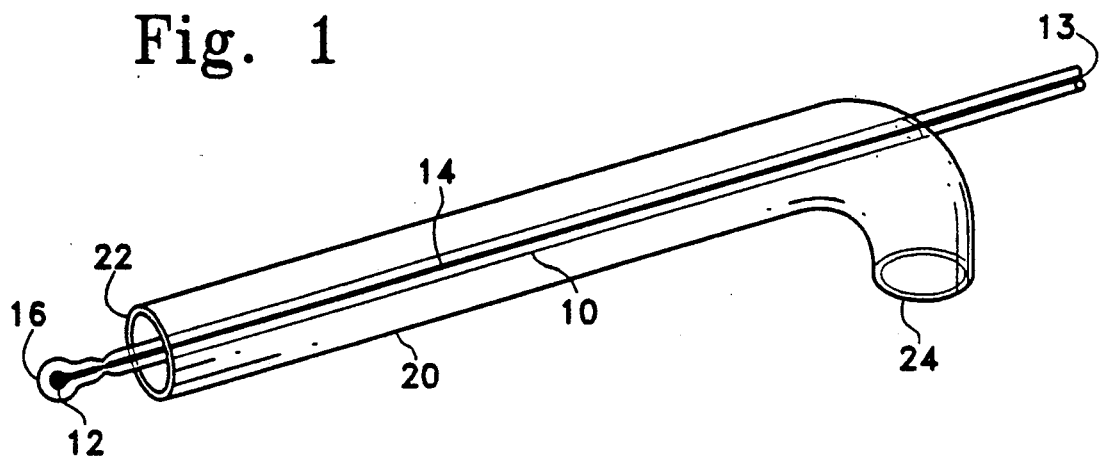
FIG. 1 is a combined electrode and coaxial delivery catheter.

The device of the subject invention provides for delivery of a vapor to neuroepithelial tissue and measurement of the change in voltage of the stimulated tissue. Preferably the device will be able to continuously and simultaneously provide a vapor and monitor the response. A vapor is the gaseous state of a substance and also a mixture of a liquid and a gas.

A. The Device

The principal elements of the device comprise sensing means for measuring electrical potential of neuroepithelium and delivery means for providing a vapor to the neuroepithelium.

1. The Electrode

Sensing means for measuring electrical potential is preferably an electrode 10 with a recording end 12 for contacting the target tissue and detecting a voltage, and an amplifier end 13 with a means for attaching the electrode 12 to a signal amplifier 17. The electrode 10 may be made of any conducting metal, preferably silver (Ag), more preferably a chlorided silver (Ag-AgCl). A Ag-AgCl electrode provides a stable voltage baseline and a high signal to noise ratio under physiological conditions. Chloriding the electrode also makes the wire non-polarizable and enables both the reference electrode and recording electrode to be at the same potential during recording. The electrode diameter is at least 0.05 mm, but no more than 0.3 mm, preferably at least about 0.1 mm but no more than about 0.2 mm. The recording end 12 of the wire may be a slightly larger diameter to provide a larger surface for contacting the tissue. This is accomplished for instance by melting the tip in a oxygen-acetylene flame to for a ball about 0.25 mm to about 0.4 mm in diameter. A method for preparing AgCl electrodes is provided infra. The length of the electrode 10 is generally no less than 50 mm and no greater than 150 mm, preferably no less than 75 mm and no greater than 125 mm.

A preferred feature of the electrode 10 is an insulating coat 14 which isolates all but 1 to 4 mm of the recording end 12 of the electrode. The insulating coat reduces electrical artifacts and permits measurement of voltage only from the exposed recording end 12. The inner diameter of the insulating coat is such that it fits snuggly around the wire electrode. The outer diameter should be as small as possible to accommodate the electrode, preferably about 0.2 mm to about 0.4 mm. The coat 14 covers the electrode wire from the means for attaching the electrode to the amplifier to near the recording end 12, usually from about 0.5 mm to 5 mm from the recording end 12. The insulating coat 14 may be made of any non-conducting material but is preferably made of polytetrafluorethylene (Teflon).

Another preferred feature of the electrode is a gelatin-saline tip 16 which provides an interface for a more conductive contact between the target tissue and the recording end 12 of the electrode. The gelatin-saline tip may be applied as a coating on the recording end of the electrode wire. Alternatively, the insulating coat 14 may extend beyond the end of the electrode forming a mold which is filled with gelatin-saline material thereby providing the gelatin-saline tip 16. The gelatin may be agarose, acrylamide or the like, or any combination of such materials. The saline solvent may be any monovalent physiologic salt such as NaCl or KCl, preferably NaCl, and the gelatin-saline mixture is prepared, as known to those skilled in the art, at generally physiologic salinity. Preferably the gelatin-saline is 4% to 7% agarose, preferably about 6% agarose, in a physiological saline. Preferably the agarose is applied by preparing a melted solution of agarose in saline and dipping the tip of the electrode no more than 3 times into the solution before the agarose can harden on the electrode. The gelatin interface reduces the chance of damaging mucosal tissue and reduces diffusion of metal ions to the cells.

2. The Delivery Catheter

Delivery means for providing a vapor to the neuroepithelium is preferably a delivery catheter 20 affixed or tethered in some fashion to the sensing means 10 such that the region of neuroepithelium measured by the sensing means is a subset of the region stimulated by the vapor. The catheter 20 is made of a flexible inert material, preferably Teflon. The outer diameter of the delivery catheter is from 2 times to 6 times larger than the insulating coat 14, or about 0.5 mm to about 2.5 mm. Preferably the outer diameter of the delivery catheter 20 is about 1 mm. The delivery catheter 20 has an output end 22 and an input end 24. The output end 22 is proximal to the recording end 12 of the electrode 10 and does not extend beyond the recording end 12. More preferably, the output end 22 is somewhat recessed from the recording end 12 of the electrode 10 at least 1 mm but no more than 5 mm, preferably at least about 2 mm but no more than about 3 mm. This reduces the possibility that the delivery catheter would interfere with the quality of contact between the electrode and the tissue. The input end 24 is coupled to vapor delivery means 25. Such means are known to those skilled in the art of neurophysiology.

The delivery catheter 20 may be immediately adjoining the electrode 10 or preferably, partially or wholly encircling the electrode. For example, the electrode 10 may be affixed along the exterior or interior wall of the delivery catheter 20. The delivery catheter 20 may be distorted to wrap around the electrode 10 creating a C-shaped catheter lumen. In a preferred embodiment, FIG. 1, the delivery catheter 20 and electrode 10 are generally coaxial and the delivery catheter surrounds the electrode from the output end 22 back at least 50 mm but no more than 150 mm, preferably about 75 mm to 125 mm. At this point the electrode 10 exits the delivery catheter 20. The area of exit on the catheter 20 can be sealed by a sealing means such as a contact cement, adhesive and the like.

In an embodiment of the invention the device comprising the sensing means 10 and delivery means 20 is intended for use within the lumen of a human VNO. Since the pit of the VNO is no more than about 1 to 2 mm and the depth of the pit about 10 mm, therefore both the recording end 12 of the sensing means 10 and the output end of the delivery means 20 must be able to be accurately inserted into the lumen of the VNO, spatially oriented to each other and to the target tissue as described, and function as described herein.

3. Evacuation Catheter

An embodiment of the device additionally comprises evacuation means for removing the vapor from the proximity of the target neuroepithelial tissue. Evacuation means is preferably an evacuation catheter 30 which is affixed or tethered in some fashion to the delivery catheter 20 such that evacuation catheter 30 scavenges vapor provided by the delivery catheter 20 in order to limit the dispersal of the vapor. The evacuation catheter 30 is made of any flexible inert material, preferably Teflon. The evacuation catheter has an scavenging end 32 and an expelling end 34. The scavenging end 32 is proximal to the output end 22 of the delivery catheter 20 and does not extend beyond the output end 22. Preferably, the scavenging end 32 is recessed from output end 22 of the delivery catheter 20 by at least 1 mm but no more than 5 mm, preferably at least about 2 mm but no more than about 3 mm. This reduces the possibility that vapor would stimulate other neuroepithelial tissue, thereby possibly confusing the interpretation of the tissue response, and in addition reduces the possibility of systemic ingestion of the vapor.

Figure 2:
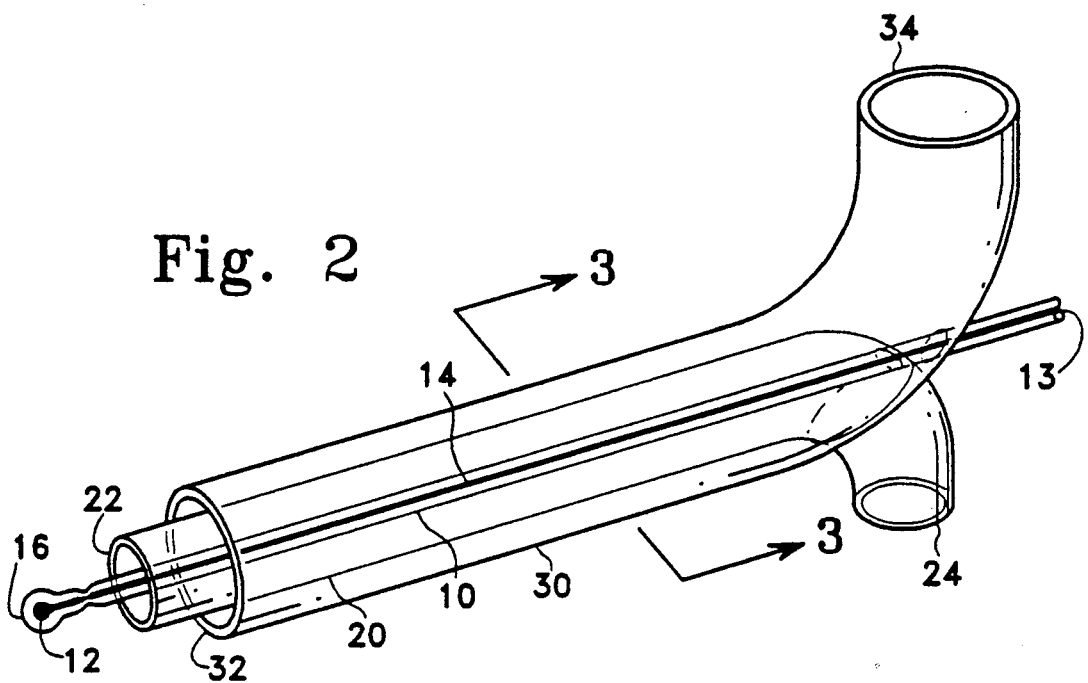
FIG. 2 is a combined electrode, coaxial delivery catheter, and coaxial evacuation catheter.
Figure 3:
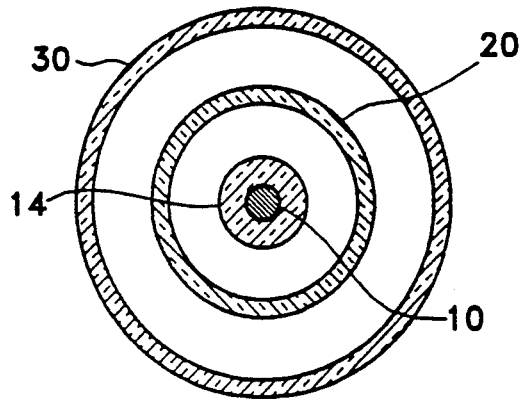
FIG. 3 is a cross section of a combined device.

The evacuation catheter 30 may be immediately adjoining the delivery catheter 20 or preferably, partially or wholly encircling the delivery catheter. In a preferred embodiment, FIGS. 2 and 3, the evacuation catheter 30 and delivery catheter 20 are generally coaxial and the evacuation catheter surrounds the delivery catheter. In a more preferred embodiment, the electrode 10, delivery catheter 20, and evacuation catheter 30 are all generally coaxial. The electrode 10 generally is central; the delivery catheter 20 surrounds the electrode 10 and the output end 22 is recessed from the recording end 12 of the electrode 10; and the evacuation catheter 30 surrounds the delivery catheter 20 with the scavenging end 32 of the evacuation catheter 30 recessed from the /utput end 22 of the delivery catheter 20.

The outer diameter of the evacuation tube 30 is preferably at least generally equivalent to and no more than 3 times larger than the outer diameter of the delivery tube 20. In the preferred embodiment wherein the delivery tube 20 evacuation tube 30 are concentric, the outer diameter of the evacuation tube is about 2 times larger than the outer diameter of the delivery tube.

In another embodiment of the invention the device comprising sensing means 10, delivery means 20, and evacuation means 30 is intended to stimulate and measure neuroepithelial tissue within the pit of a human VNO. Since the opening of the VNO is no more than about 1 to 2 mm and the depth of the pit about 10 mm, therefore both the recording end 12 of the sensing means 10 and the output end of the delivery means 20 is insertible into the VNO, they can be spatially oriented to each other and to the target tissue as described, and they function as described herein. Furthermore, the scavenging end 32 of the evacuation means 30 can be spatially oriented proximal to and just outside of the opening to the vomeronasal pit such that the vapor delivered by the delivery means 20 within the pit is removed by the evacuation means 30 as it exits the vomeronasal pit.

2. Peripheral Equipment

The device of the subject invention is intended to function as a component in combination with several instruments, devices and means known to those skilled in the art and/or readily available from commercial sources.

A. Amplifying Means

Figure 5A:
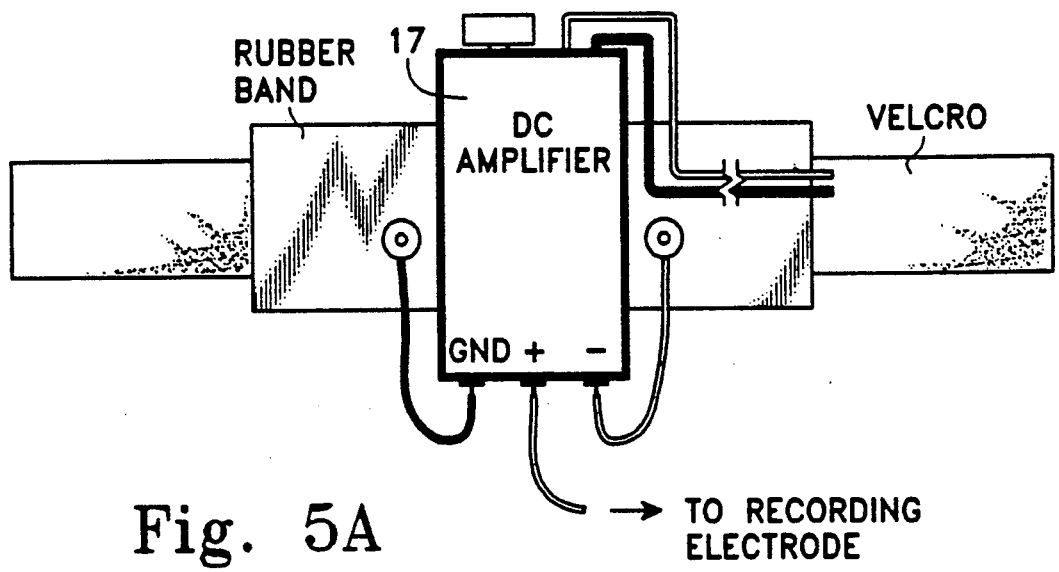
FIGS. 5A depicts an amplifier and 5B depicts the positioning of the amplifier on a human subject.
Figure 5B:
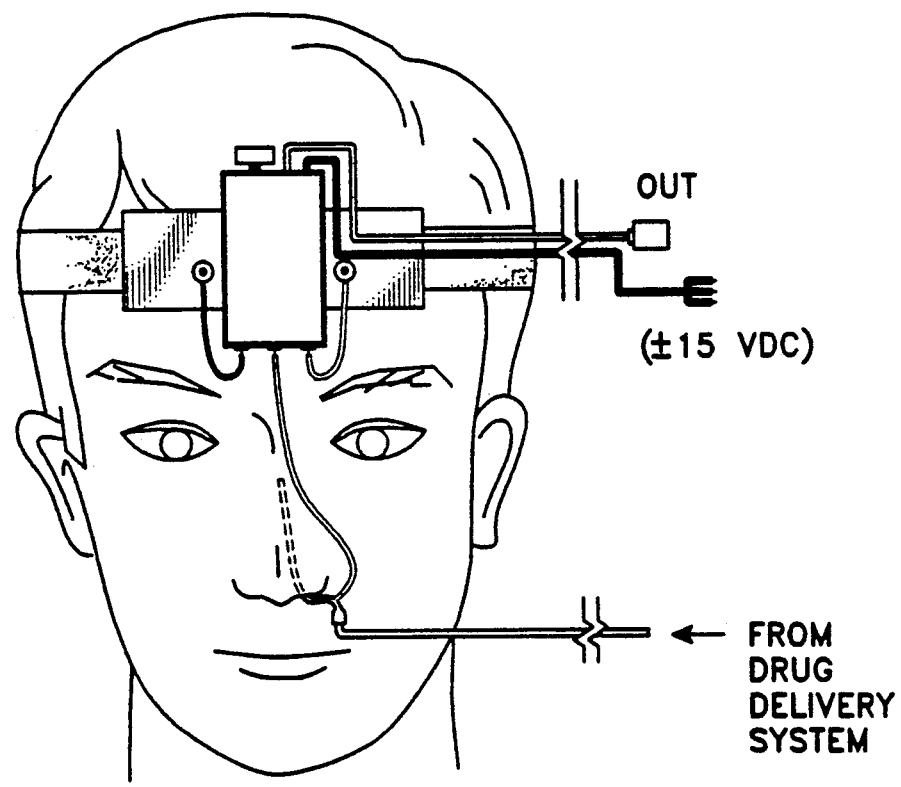

The amplifier end 13 of the sensing means 10 is coupled to amplifying means 17 for enhancing the signal from the neuroepithelial tissue. This type of signal amplification is well known to those skilled in the art of neurophysiology. In an embodiment, amplifying means is a DC amplifier 17, preferably a low noise amplifier such as the one shown in FIG. 5. The BB-INA 110 (Bur-Brown Inc.) is an acceptable amplifier. Short cables are preferred between the amplifier 17 and the electrode 10, and between the amplifier 17 and reference electrode, to reduce artifacts.

In an embodiment the device is used to stimulate and monitor changes in nasal neuroepithelia of an individual. In a preferred embodiment, FIG. 5, the amplifier is strapped to the forehead of the individual and the reference electrode is placed generally proximal to the glabella on the forehead.

The amplified signal goes to an oscilloscope or similar means for continuous display and/or recording of signal and time.

B. Vapor Delivery Means

The input end 24 of the delivery means 20 is coupled to vapor delivery means 25 for enhancing the signal from the neuroepithelial tissue. Vapor delivery means are well known to those skilled in the art of neurophysiology. See, for example, Tucker, D. and T. Shibuya, supra, Vigouroux, M., et al., supra. See also Frey, A. H., AD-705 520, work done under U.S. Gov. contract No. N00014-69-C0181.

In a basic form, vapor delivery means 25 is a constant air flow source bubbled through a liquid medium. The vapor may be variously regulated by a singled parameter or in combination—for instance, purity, temperature, water vapor tension, flow rate, and the like. Various stimulants, for instance an odorant, a flavoring, a drug, or the like, may be introduced into the vapor stream either continuously, or preferably, as a pulse of particular duration.

In a preferred embodiment vapor delivery means is an olfactometer 25 which is designed to deliver odorants to olfactory epithelium or vomeronasal epithelium. The olfactometer delivers a continuous mild stream of filtered air at a rate of about 15 ml to about 30 ml per minute, about 35° to about 37° C., with a water vapor tension of about 45 mm to about 50 mm Hg, preferably about 47 mm. Constant water vapor tension avoids desiccation of the nasal mucosa which in turn reduces discomfort and irritation of the subject.

Figure 4:
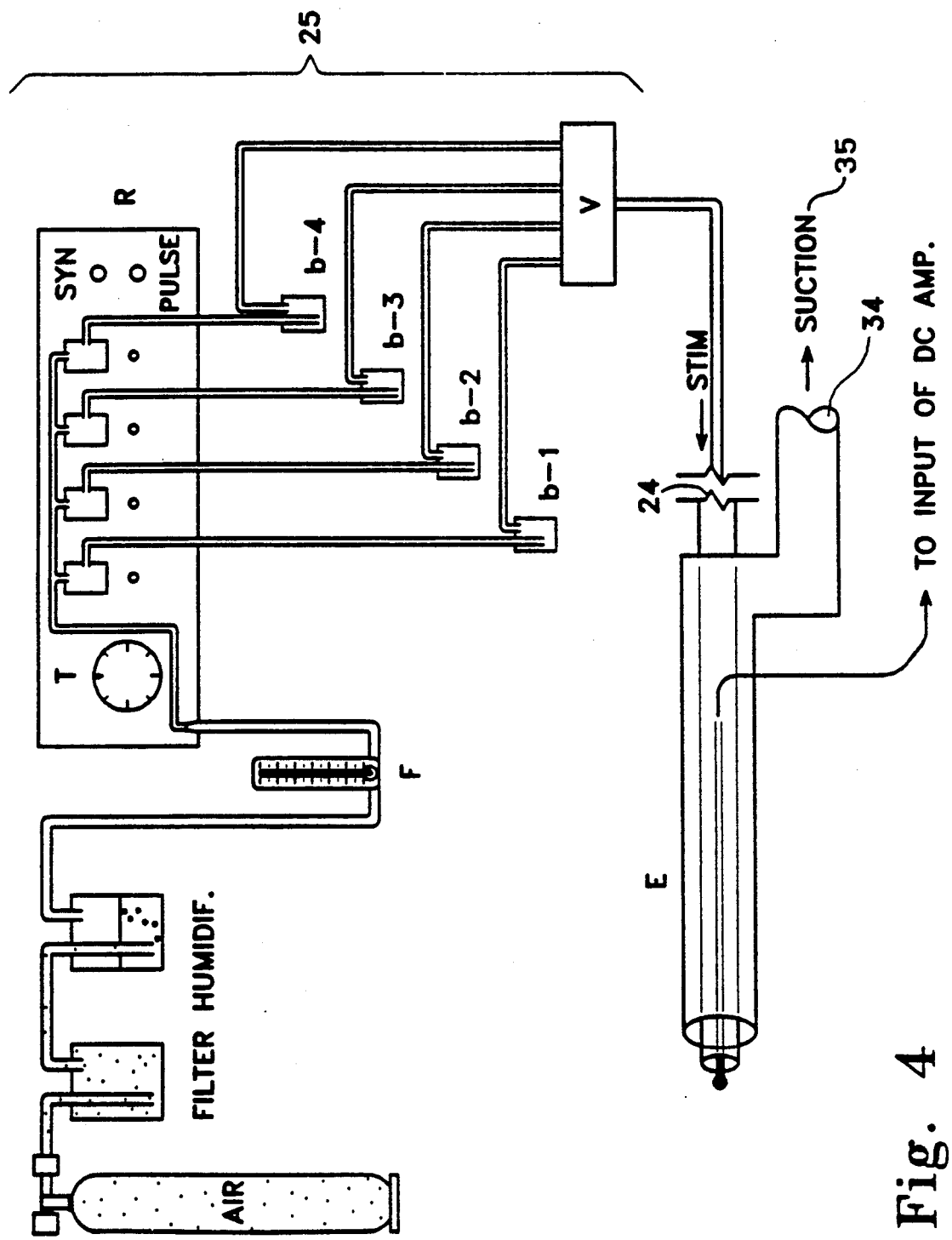
FIG. 4 is a combined device with a multichannel osmometer.

In a more preferred embodiment, the olfactometer is multichannel as shown in FIG. 4. The default channel is as described above. The remaining channels are used to deliver odorant or pheromonal substances in a vaporous form. The device can be controlled electronically by means which are commercially available. Preferably the channels can be rapidly switched without interrupting the continuous air flow. This permits testing of several substances in sequence. Each substance is delivered in a short pulse followed by a flushing period and then the delivery of another substance.

C. Suction Means

The expelling end 34 of evacuation means 30 is coupled to suction means 35. Suction means is any source of suction or vacuum, preferably a source which can be regulated and maintain a steady draw, more preferably a non-electrical means such as a water aspirator. The rate of suction is at least 50 ml/min. but no more than 500 ml/min, preferably about 150 ml/min.

3. Methods of Use

Certain embodiments of the subject invention are methods of using the devices of the invention to deliver vapor to a specific locus of neuroepithelial tissue of a subject, and measure the response of the stimulated tissue. With regard to the locus of tissue stimulated and measured, these methods provide a greater degree of precision and accuracy than has been possible heretofore. Consequently, this method also uniquely provides the ability to stimulate and measure very small loci of tissue. This method also for the first time provides the ability to stimulate and measure the neuroepithelial tissue within the pit of a mammalian, preferably a human, vomeronasal organ—a tiny cul-de-sac in the nasus tissue.

Generally, the method is as follows. The device is attached to vapor delivery means 25 and amplifying means 17, and if appropriate, suction means 35, and the recording end 12 of the electrode is visually placed in contact with the target tissue. This is usually done manually and visually, but can be done with magnifying means known to those skilled in the art of microsurgery. Even in the case of vomeronasal measurement the device is simple and compact enough that it can easily be visually placed within the pit of the VNO.

Preferably delivery means is an olfactometer, a device which provides a regulated stream of gas, usually air, and bubbles the gas through a liquid creating a vapor. Usually the air stream is filtered and temperature controlled, and the duration of the vapor pulse can also be regulated. A multichannel olfactometer further comprises a series of switches which allows the stream of air to be directed into one or more of a variety of liquids, usually each containing a different substance in solution.

A vapor stream is provided, preferably on a constant basis, at a rate of about 15 to 30 ml/min, more preferably about 20 ml/min. A stimulant appropriate for the target tissue is introduced as a brief pulse, usually about 500 msec. If the vapor delivery means is a multichannel osmometer, a series of pulses representing different stimulants are introduced. The electrode records voltage relative to a reference electrode on a continuous basis. The reference electrode is placed proximal to the neuroepithelial tissue being measured. For instance, when nasal neuroepithelia is measured, the reference electrode is usually placed on the glabella of the subject. The amplified signal is continuously monitored on an oscilloscope or similar device and is permanently recorded on a paper readout.

In another embodiment, the device of the method described above also has an evacuation means. The scavenging end 32 of evacuation means is positioned such that it continuously scavenges the vapor such that the most of the vapor does not diffuse from the target tissue after stimulation.

In yet another embodiment a method of stimulating and measuring vomeronasal neuroepithelium is provided. This method comprises the steps described above; however, the dimensions of the device of the method are such that device fits within and is easily placable within the vomeronasal nasal organ. Usually the diameter of the combined device is no greater than about 1 mm. In another embodiment the combined device, additionally comprising an evacuation means, is used to measure vomeronasal neuroepithelial potential. The delivery and recording elements of the device of this method are placed in the vomeronasal organ as above. The scavenging end 32 of the evacuating means is located proximal to but outside of the vomeronasal pit. Thus, the evacuation means scavenges most all vapor escaping from the vomeronasal organ.

D. Methods of Preparing Chlorided Silver Electrodes

1. Clean the silver wires with commercial alcohol and let dry for 5 minutes.

2. Connect each silver wire to a 22.5 kOhm resistor. Place the silver wires in a beaker containing a generous volume of 0.2 Molar NaCl. Immerse at least 2 cm of the wire length in the solution.

3. Using a carbon rod as a cathode apply a 9 volt DC current to the anode wires for 30 minutes.

Take the electrodes out of the beaker and let them dry in air for 10 minutes.

If the chlorided electrodes appear to be drifting, they can be touched up by immersing them in a 5% Na-hypochlorite solution for 10 to 15 minutes.

The following example illustrates an embodiment of the invention and is not intended to limit the invention in any way.

E. Example

Effects of Putative Pheromones on the Electrical Activity of the Human VNO and Olfactory Epithelium The summated receptor potential was recorded from the VNO and olfactory epithelium (OE) of 49 human subjects of both sexes (18 to 55 years old) using surface non-polarizable silver-silver chloride electrodes. Fifteen to 25 pg of putative human pheromones, clove oil and a diluent were administered to the VNO or the OE in 0.3-1.0 second pulses from a 0.05 mm diameter delivery catheter connected to a multichannel delivery olfactometer. Local stimulation of the VNO produces negative potentials of 1.8-11.6 Mv showing adaptation. Responses were not obtained when the recording electrode was placed on the nasal respiratory mucosa.

1. Method

The study was performed in 49 clinically normal individuals without the use of anesthetics. A schematic diagram of the stimulating system. The system includes a combined device which is an embodiment of the subject invention, and a multichannel olfactometer. The device comprises a central electrode, a coaxial delivery catheter which surrounds the electrode, and a coaxial evacuation catheter which surrounds the delivery catheter. The device is 100 mm long.

The electrode was a chlorided Ag wire of 0.08 mm diameter. The wire was surrounded with an insulating Teflon coat (AM Systems) except for the last 2 mm of the recording tip. The tip had been melted in an oxygen-acetylene flame to form a bare 0.3 mm ball and the surface of the ball was coated with a gelatin-epithelium interface of 6% agarose in physiologic saline.

The insulated Ag-AgCl electrode was positioned generally coaxial within a 100 mm Teflon delivery catheter (O.D.=1 mm) such that the chlorided recording end protruded about 1 mm beyond the output end of the delivery catheter while the amplifier end was connected to a D.C. low noise amplifier (BB-INA 110, Bur-Brown Inc.).

The input end of the delivery catheter was connected to a multichannel olfactometer which delivered pulses of vaporous air sequentially from multiple chambers containing various pheromones in diluent.

The delivery catheter was positioned generally coaxial with a second Teflon catheter referred to as the evacuation catheter (O.D.=2 mm). The expelling end was connected to an aspirator that provided a continuous suction at the suction end of the evacuation catheter of about 0.3 ml/sec. When the electrode and delivery catheter were positioned in the lumen of the VNO, the suction end of the catheter remained outside but proximal to the pit of the VNO. This allowed all vapor escaping from the VNO to be scavenged immediately by the evacuation catheter. This concentric configuration allowed chemical stimulation to be localized within the VNO and avoided diffusion of stimulatory substances to neighboring olfactory tissue or into the respiratory system.

Recording was carried out in a quiet room with the supine subject lying on a bed with a small pillow under the neck to allow comfortable neck extension. Reference and ground electrodes were chlorided silver discs (diameter=8 mm). The reference electrode attached on the glabella, and the ground electrode was attached over the mastoid process using Redux Gel (Hewlett Packard) and adhesive hypo-allergenic discs. The pit of the VNO was identified close to the intersection of the posterior edge of the septal cartilage and the nasal floor by opening the right nare using a nasal speculum.

The Teflon delivery catheter and recording electrode were then gently introduced past the VNO pit into the lumen for a distance of 1-3 mm and held in place with surgical hypo-allergenic tape. The nasoscope was then withdrawn. During recording the subject were asked to breathe through the mouth. Local anesthetics were not required and the subjects reported little discomfort.

Electrical potentials from the D.C. low-noise amplifier were digitized (sampling rate—100 Khz) (MacLab/4, World Precision Instruments, Inc.) and stored utilizing an on-line computer (Mackintosh SE30, Apple). The peak-to-peak amplitude of the locally recorded electrical potentials were then measured and also their area integrated. Measurements were continuously monitored both on the computer screen and on a digital oscilloscope. Electrical or mechanical artifacts caused by movement of the subject, deep breathing swallowing or blinking, etc. were deleted.

Test substances included diluent, a clove oil (Sigma), putative pheromones ER-670, ER-830, ER-700, ER-795 and ER-360 (EROX Corp.) Samples were diluted in concentrations of 15-25 pg and loaded in separate chambers. Clean humidified air vapor at 34° C. was continuously bubbled sequentially through each container. A chemical stimulus consisted of pulses of saturated air vapor lasting 300, 500, or 100 mSec. Usually an interval of at least 5-10 minutes separated each series of air pulses.

Recordings from the OE employed the same stimulating device and system. The recording tip of the recording electrode was positioned in the lateral part of the medial nasal duct and slowly introduced until it reaches the OE. Adequate contact was signaled by local depolarization in response to odorous test stimuli which were the same as those used for stimulation of the VNO.

2. Results

Figures 6A, 6B:
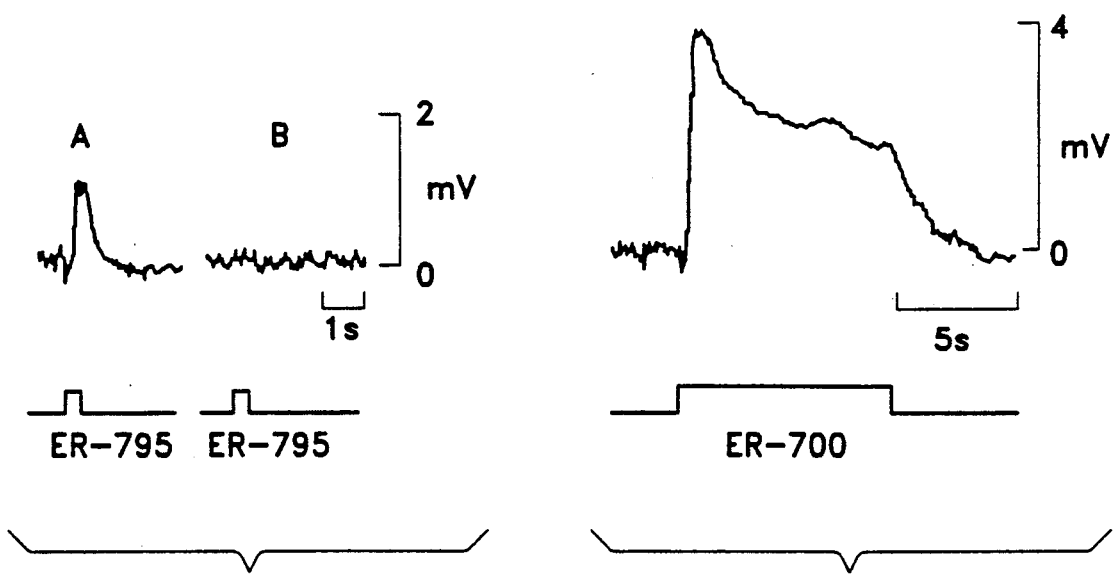
FIGS. 6A-C are graphic representations of characteristics of the receptor potential recorded from the human VNO using a combined delivery/electrode.
Figure 6C:
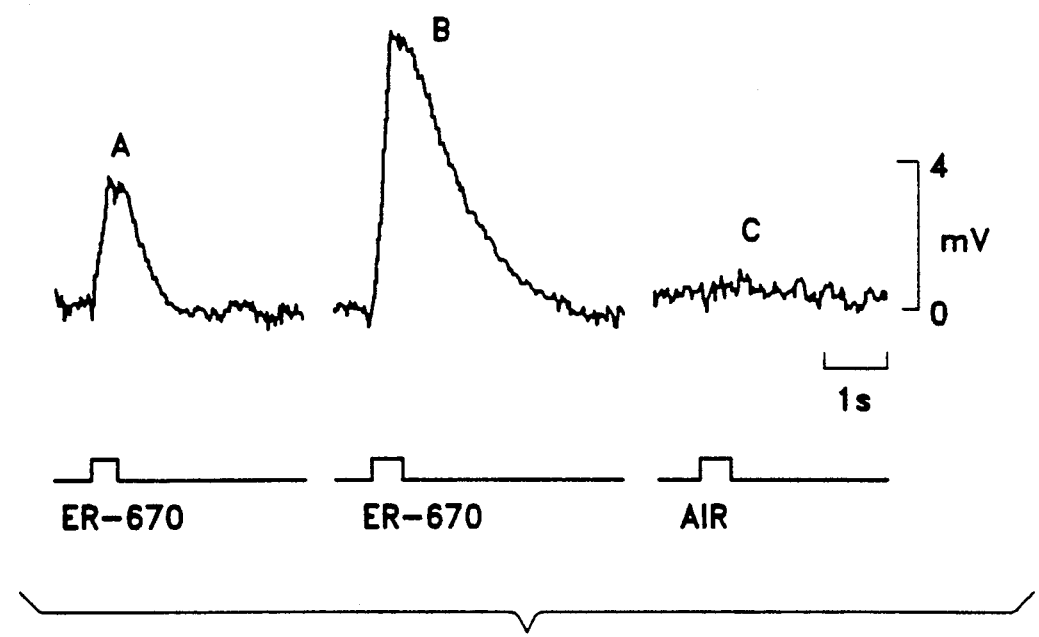

As shown in FIG. 6(I-A), a typical negative potential was produced by local stimulation with 25 pg of putative pheromone ER-795 and was recorded from the VNO of a 31-year old woman. Depolarization rises steeply reaching a peak at 2 mV and decaying to baseline with a slower slope. The long latency of the potential (200 mS after application of the stimulus) is probably due in large part to the time required for arrival of the stimulus at the receptors.

If the combined delivery/electrode device is positioned in nearby respiratory mucosa, stimulation produces no effect, FIG. 6(IB). A response is also absent when the device is in contact with the VNO epithelium and stimuli are applied either to the OE or nasal respiratory mucosa by means of a mobile cannula. Thus, the VNO negative potential is produced by specific chemosensory stimuli delivered to the sensory epithelium of the VNO.

As shown in FIG. 6(II), a prolonged (10 sec.) pulse of vapor containing ER-700 (25 pg) induced transient depolarization, followed by a plateau and slow decay during maintenance of the stimulus. This demonstrates adaptation of the receptors to the stimulus, a characteristic of all receptor cells. VNO receptors also show adaptation to stimulation with repetitive pulses of short duration. Therefore, the potentials recorded from the VNO epithelium have similar properties to the summated receptor potentials from depolarized groups of receptor cells in other organs.

The size of the potential recorded from the VNO is a function of stimulus strength. As shown in FIG. 6(III), the right VNO of a 42-year old woman was stimulated with vapor pulses produced by different concentrations of pheromone ER-670. Trace A shows the response to a 500 mSec. pulse of low concentration (15 pg). This stimulus produced a negative potential with a steep rising phase, followed by a slow decay toward the baseline. In trace B, a second pulse containing a higher concentration (25 pg) was delivered which produced a larger response with a steeper rising phase. Also, the duration of the response was increased. In trace C, a pulse of vapor alone induced an insignificant change in potential.

The absence of a response to vapor alone shows that the potentials recorded in traces A and B are biological events produced in response to chemical stimulation of the receptors and are not due to artifacts induced by mechanical stimulation.

Figure 7:
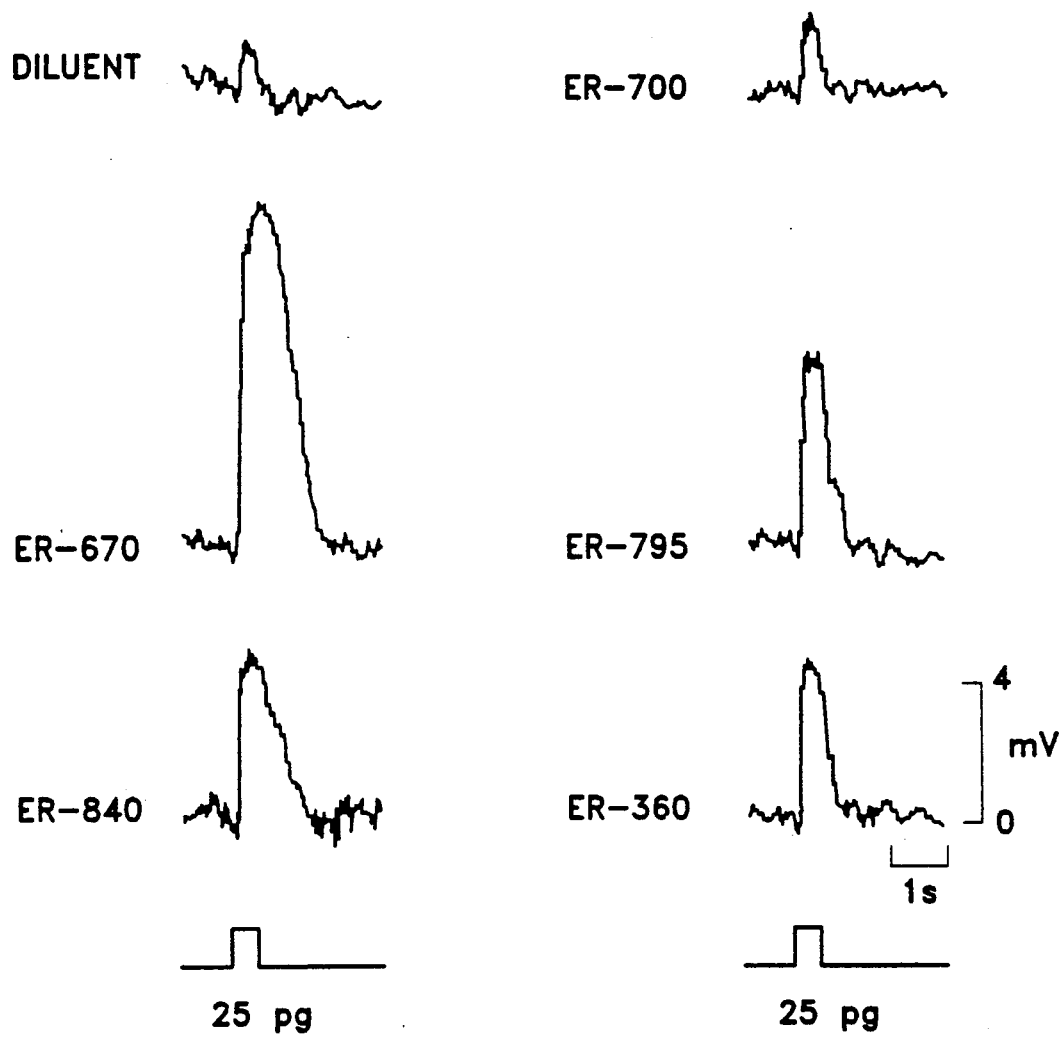
FIG. 7 are oscilloscopic tracings of amplified receptors potentials responding to various pheromone stimuli.

Evidence that the character of the rising phase of the negative potential is a function of qualitative differences between the pheromonal stimuli is provided in FIG. 7. Here the concentration of pheromone was adjusted to 25 pg. Stimuli were presented to the VNO at 5 minute intervals to allow full recovery between applications and all stimuli were delivered as 500 mSec. pulses. Responses, differing in amplitude but with similar rising phases, follow each stimulus. On the other hand, the recovery phase of these potentials recorded from the VNO epithelium has a characteristic signature in response to each stimulus.

Figure 8:
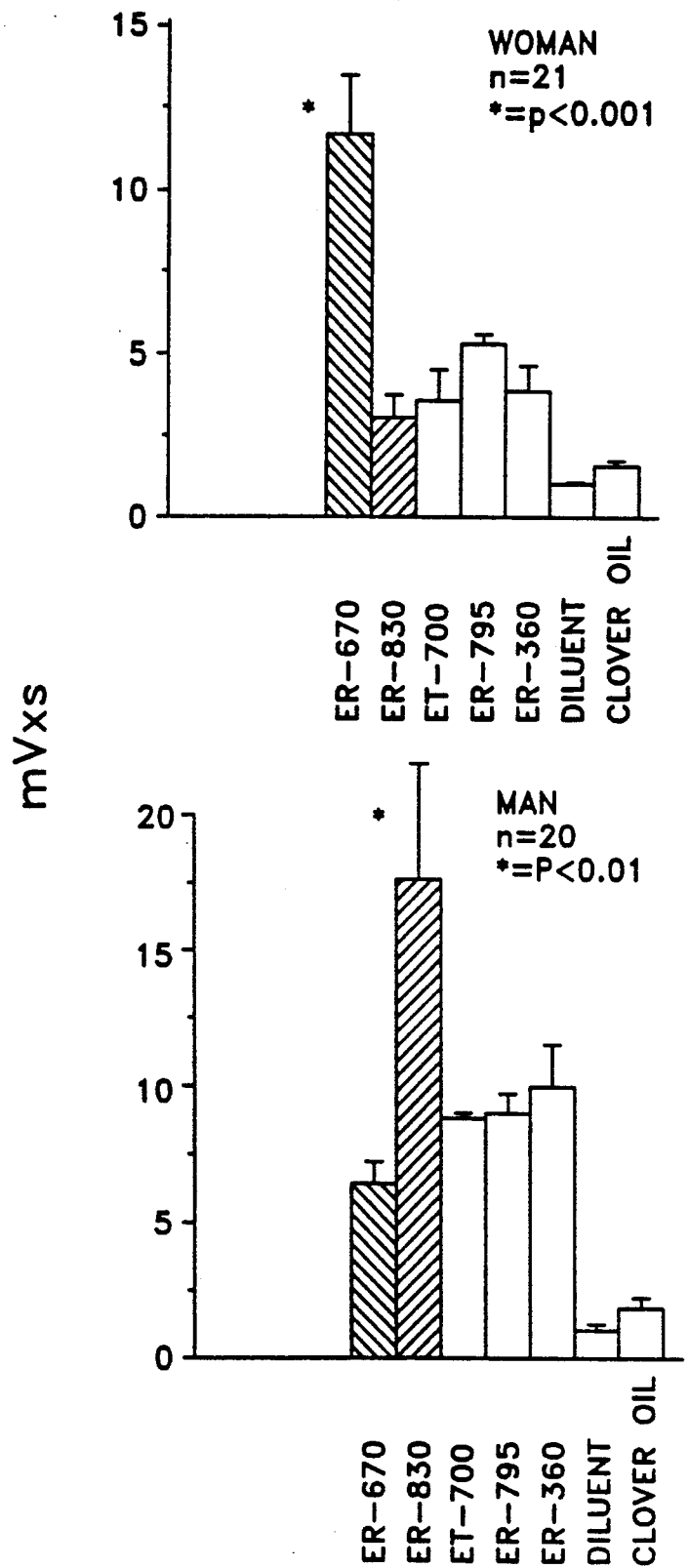
FIG. 8 are bar graph representations of the summated responses of of the human VNO to various stimuli in females (I) and in males (II).

For many of the pheromones tested it was noted that the receptor potential varied depending on the sex of the subject. Thus, experiments were conducted to study the difference of VNO response in male and female subjects. Examples are shown in FIG. 8(I and II) and also in Table I.

Recordings of the electrovomeronasogram (EVG) were done in a population of 20 women (18 to 55 years old), divided into two groups: 17 fertile women in the preovulatory stage of their menstrual cycle; and 3 menopausal subjects (see Table I). Test odorant, diluent and pheromones were diluted and applied to the VNO in 1 second pulses at 5 minute intervals. FIG. 8 shows the averaged response of the female subjects to a classic odorant (clove oil), to the diluent, and to 5 pheromones (ER-670, ER-830, ER-700, ER-795, ER-360). The profile of the response to each of the substances was similar in all subjects regardless of age. No significant differences were revealed by t-tests and ANOVA. For example, ER-670 produced a significant effect that was consistent in all individual cases. Other pheromones depolarized the VNO receptors to a lesser extent. with consistent mean response amplitudes from individual to individual. All pheromones produced larger responses than did the diluent alone or the olfactant clove oil.

TABLE 1

| | Effect of human pheromones | | | |
|---|---|---|---|---|
| | Mean | | SEM | |
| Substance | Male | Female | Male | Female |
| ER-670 | 6.6 | 11.45 | 1.13 | 1.49 |
| ER-830 | 18.2 | 2.96 | 4.4 | 0.52 |
| ER-700 | 9.05 | 3.47 | 0.15 | 0.74 |
| ER-795 | 9.1 | 5.12 | 0.7 | 0.41 |
| ER-360 | 10.1 | 3.79 | 1.55 | 0.79 |
| DILUENT | 1.14 | 0.86 | 0.3 | 0.12 |

TABLE 1-continued

| | Effect of human pheromones | | | |
|---|---|---|---|---|
| | Mean | | SEM | |
| Substance | Male | Female | Male | Female |
| CLOVE OIL | 1.9 | 1.53 | 0.4 | 0.14 |

A similar experimental protocol was followed with 20 male subjects whose ages ranged from 25 to 45 years (FIG. 8-II). Among the pheromones, ER-830 produced the most significant effect with no significant differences within the group. The mean response amplitudes to clove oil and to diluent alone are similar in male and female subjects, and none of the male subjects reported detecting odor of the test substances.

Figure 9:
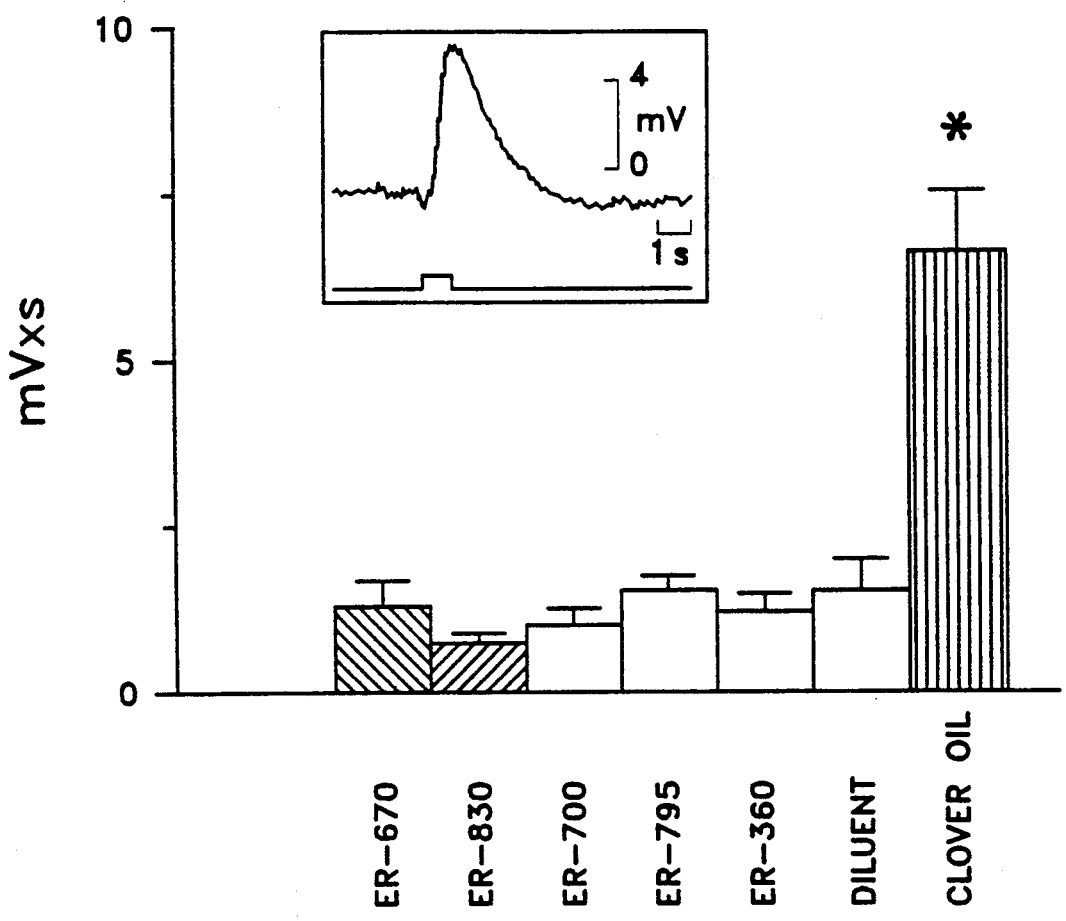
FIG. 9 is a bar graph representation of the summated responses of the olfactory epithelia of a human subject to various odorants and pheromones.

The summated receptor potential from stimulation of the OE was recorded in 9 human subjects: 3 males and 6 females. As described above, all substances were tested at the same concentration (25 pg) and were delivered in 1 second pulses. However, in the experiments they were intercalated with a continuous flow of vapor (0.3 ml/sec.). The inset in FIG. 9 shows a typical olfactory potential recorded from a 37-year old man following stimulation with clove oil. Stable recordings were obtained from the olfactory mucosa in all subjects utilizing this traditional olfactant. The chart in FIG. 9 shows the mean effect produced in 9 subjects by the 5 pheromones, the diluent alone, and by clove oil. Stimulation with clove oil produced a large response similar to those previously described. This was accompanied by a clear olfactory sensation in all subjects. While diluent depolarized the olfactory receptors to a lesser extent than clove oil, it also produced an olfactory sensation in all subjects. In contrast the putative pheromones have a minimal effect on the olfactory epithelium. The mean of the effects ranged from 0.79 to 1.58 mV×Sec.

Modifications of the disclosed modes for carrying out the invention that are obvious to those of skill in neurophysiology, scientific instrumentation and related fields are intended to be within the scope of the following claims.

I claim as may invention:

1. A device for delivering a vapor to neuroepithelial tissue and measuring the neurophysiologic response of the tissue, said device comprising:
   delivery means with an output end for continuously providing the vapor to a locus of neuroepithelial tissue; and
   sensing means with a recording end proximal to the output end for simultaneously measuring bioelectrical potential from tissue within said locus.

2. The device of claim 1 wherein said locus of tissue is within a vomeronasal pit of a human subject.

3. A device for delivering a vapor to neuroepithelial tissue and measuring the neurophysiologic response of the tissue, said device comprising:
   an electrode means for continuously measuring the bioelectrical potential from tissue within a locus of neuroepithelial tissue, said electrode means having a recording end; and
   a delivery means for continuously delivering the vapor to said locus, said delivery means comprising a catheter, said catheter being coaxial with and surrounding the electrode means, and having an output end proximal to the recording end of the electrode means.

4. The device of claim 3 wherein the output end of the delivery means is recessed from the recording end of the electrode means.

5. The device of claim 3 wherein the delivery catheter is made of Teflon.

6. The device of claim 3 wherein the diameter of the delivery catheter is no greater than 1.5 mm.

7. The device of claim 6 wherein the diameter of the delivery catheter is no greater than about 1 mm.

8. The device of claim 3 additionally comprising evacuation means for removing the vapor from the proximity of neuroepithelial tissue.

9. The device of claim 8 wherein said evacuation means comprises an evacuation catheter coaxial with and surrounding the delivery catheter, said evacuation catheter having a scavenging end proximal to the output end of the delivery catheter.

10. The device of claim 9 wherein the scavenging end of the evacuation catheter is recessed from the output end of the delivery catheter.

11. The device of claim 9 further comprising an insulating coat which covers all but the recording end of the electrode means.

12. The device of claim 11 wherein the insulating coat is made of Teflon.

13. The device of claim 11 further comprising a gelatin tip at the recording end of the electrode means.

14. The device of claim 13 wherein the gelatin comprises agarose.

15. The device of claim 13 in which the electrode means comprises a AgAgCl wire.

16. The device of claim 9 in which the diameter of the delivery catheter is no greater than 1.5 mm and the diameter of the evacuation catheter is no greater than 3 mm.

17. The device of claim 16 in which the diameter of the delivery catheter is no greater than about 1.0 mm and the diameter of the evacuation catheter is no greater than about 2 mm.

18. The device of claim 16 wherein the diameter of the electrode means is about at least about 0.1 mm but no more than 0.3 mm.

19. The device of claim 18 wherein the diameter of the electrode means is about 0.2 mm.

20. The device of claim 18 further comprising amplifying means for amplifying the measurement of bioelectric potential detected by the electrode means.

21. The device of claim 20 wherein amplifying means comprises a DC low noise amplifier.

22. The device of claim 20 further comprising vapor delivery means for providing the vapor to the delivery catheter.

23. The device of claim 22 wherein vapor delivery means comprises an osmometer.

24. The device of claim 22 further comprising suction means for providing a vacuum to the evacuation catheter.

25. A method of delivering a vapor to neuroepithelial tissue within a human vomeronasal pit and measuring the neurophysiologic response of the tissue, comprising the step of:
providing the device of claim 2;
placing the output and recording ends of the delivery means and sensing means within the vomeronasal organ;
continuously delivering the vapor via the delivery means within the pit; and
simultaneously recording the bioelectric response with the sensing means.

26. A method of delivering a vapor to neuroepithelial tissue of a subject, measuring bioelectric response, and removing the vapor, said method comprising the step of:
providing the device of claim 24
placing the recording end of the electrode means in contact with a neuroepithelial tissue;
delivering the vapor through the delivery catheter;
recording the bioelectric response with the electrode means; and,
removing the vapor through the evacuation catheter.

27. The method of claim 26 wherein the delivery, recording, and evacuation are continuous.

28. The method of claim 27 in which the tissue is nasal neuroepithelium.

29. The method of claim 28 in which the subject is a mammal.

30. The method of claim 29 in which the mammal is human.

31. The method of claim 30 in which the tissue is olfactory neuroepithelium.

32. The method of claim 31 in which the vapor contains an odorous compound.

33. The method of claim 30 in which the tissue is vomeronasal neuroepithelium.

34. The method of claim 33 in which the vapor contains a human pheromone.

* * * * *

UNITED STATES PATENT AND TRADEMARK OFFICE
CERTIFICATE OF CORRECTION

PATENT NO. : 5,303,703    Page 1 of 2
DATED     : Apr. 19, 1994
INVENTOR(S) : Luis Monti-Bloch It is certified that error appears in the above-indentified patent and that said Letters Patent is hereby corrected as shown below:

On drawing sheet

In Figure 8 of the drawings, delete "Clover Oil" which appears twice, and insert --Clove Oil--.

In Figure 9 of the drawings, delete "Clover Oil" and insert --Clove Oil--.

Column 3, Line 39, delete "of of" and insert --of--.

Column 4, Line 11, delete "for" and insert --form--.

Column 6, Line 6, delete "/utput" and insert --output-.

Column 10, Line 37, delete "reaches" and insert --reached--.

Column 11, Line 47, delete "averaged" and insert --average--.

Column 11, Line 55, delete "extent." and insert --extent--.

UNITED STATES PATENT AND TRADEMARK OFFICE
CERTIFICATE OF CORRECTION

PATENT NO. : 5,303,703

DATED : Apr. 19, 1994

INVENTOR(S) : Luis Monti-Bloch

It is certified that error appears in the above-indentified patent and that said Letters Patent is hereby corrected as shown below:

Column 12, Line 43, delete "may" and insert --my--.

Signed and Sealed this

Sixth Day of September, 1994

Attest:

BRUCE LEHMAN

Attesting Officer

Commissioner of Patents and Trademarks